US010279025B2

(12) United States Patent
Sakamoto et al.

(10) Patent No.: US 10,279,025 B2
(45) Date of Patent: *May 7, 2019

(54) LPS VACCINE

(71) Applicant: THE CHEMO-SERO-THERAPEUTIC RESEARCH INSTITUTE, Kumamoto-shi (JP)

(72) Inventors: Ryuichi Sakamoto, Kumamoto (JP); Masashi Sakaguchi, Kikuchi (JP)

(73) Assignee: THE CHEMO-SERO-THERAPEUTIC RESEARCH INSTITUTE, Kumamoto-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/623,478

(22) Filed: Jun. 15, 2017

(65) Prior Publication Data

US 2017/0281745 A1 Oct. 5, 2017

Related U.S. Application Data

(60) Continuation of application No. 15/098,563, filed on Apr. 14, 2016, now abandoned, which is a division of application No. 14/385,606, filed as application No. PCT/JP2013/054038 on Feb. 19, 2013, now Pat. No. 9,345,756.

(30) Foreign Application Priority Data

Mar. 22, 2012 (JP) ................ 2012-065162

(51) Int. Cl.
| | | |
|---|---|---|
| *A61K 39/102* | (2006.01) | |
| *C12N 7/00* | (2006.01) | |
| *A61K 39/112* | (2006.01) | |
| *A61K 39/02* | (2006.01) | |
| *A61K 39/215* | (2006.01) | |
| *A61K 39/235* | (2006.01) | |
| *A61K 39/295* | (2006.01) | |
| *A61K 39/04* | (2006.01) | |
| *A61K 39/00* | (2006.01) | |
| *A61K 39/17* | (2006.01) | |

(52) U.S. Cl.
CPC ........ *A61K 39/0275* (2013.01); *A61K 39/025* (2013.01); *A61K 39/0208* (2013.01); *A61K 39/0241* (2013.01); *A61K 39/04* (2013.01); *A61K 39/102* (2013.01); *A61K 39/215* (2013.01); *A61K 39/235* (2013.01); *A61K 39/295* (2013.01); *C12N 7/00* (2013.01); *A61K 39/17* (2013.01); *A61K 2039/552* (2013.01); *A61K 2039/6037* (2013.01); *A61K 2039/70* (2013.01); *C12N 2710/10234* (2013.01); *C12N 2710/10271* (2013.01); *C12N 2770/20034* (2013.01); *C12N 2770/20071* (2013.01)

(58) Field of Classification Search
CPC ............... A61K 39/102; A61K 39/025; A61K 2039/552; A61K 39/295; A61K 39/235; A61K 2039/70; A61K 39/17; A61K 39/0275; A61K 39/0241
See application file for complete search history.

(56) References Cited

U.S. PATENT DOCUMENTS

| | | | | |
|---|---|---|---|---|
| 9,345,756 B2 * | 5/2016 | Sakamoto | ............ | A61K 39/102 |
| 2005/0260225 A1 | 11/2005 | Goldberg et al. | | |

FOREIGN PATENT DOCUMENTS

| | | |
|---|---|---|
| JP | 2001-026602 A | 1/2001 |
| RU | 2 377 015 C1 | 12/2009 |
| RU | 2 455 023 C2 | 7/2012 |
| WO | 00/04920 A2 | 2/2000 |
| WO | 2004/052394 A1 | 6/2004 |
| WO | 2005/111196 | 11/2005 |
| WO | WO 2008/073891 A2 | 6/2008 |
| WO | WO 2008/073891 A3 | 6/2008 |
| WO | 2009/046449 | 4/2009 |
| WO | 2010/082020 A1 | 7/2010 |

OTHER PUBLICATIONS

Office Action as received in the corresponding Russian Patent Application No. 2014138021 dated Jun. 22, 2017 w/English Translation.
International Search Report dated Apr. 23, 2013 in PCT/JP2013/054038 filed Feb. 19, 2013.
Ram Parkash Tiwari, et al., "Immunobiology of Lipopolysaccharide (LPS) and LPS-Derived Immunoconjugates Vaccinate Mice against *Salmonella typhimurium*" Microbiol. Immunol., vol. 42, No. 1, 1998, pp. 1-5.
Kazuhiro Deguchi, et al., "Efficacy of a Novel Trivalent Inactivated Vaccine Against the Shedding of *Salmonella* in a Chicken Challenge Model" Avian Diseases, vol. 53, 2009, pp. 281-286.
Paul A. Rebers, et al., "The Effect of Formalin-Killing of *Pasteurella multocida* on the Antigenicity and Extractability of its Lipopolysaccharide" Carbohydrate Research, vol. 133, 1984, pp. 83-94.

(Continued)

*Primary Examiner* — Padmavathi Baskar
(74) *Attorney, Agent, or Firm* — Oblon, McClelland, Maier & Neustadt, L.L.P.

(57) ABSTRACT

A vaccine composition for birds comprising as an active ingredient a structure containing O-antigen derived from Gram-negative bacteria, provided that said structure does not contain a whole cell, and a process for preparing the same are provided. By using a structure containing O-antigen (e.g. lipopolysaccharide) derived from Gram-negative bacteria as an active ingredient in accordance with the present invention, alleviation of inoculation reaction and reduction in an amount of injection are attained as compared to the conventional whole-cells vaccine to thereby allow for the increase in the number of other antigens to be mixed therewith.

10 Claims, 6 Drawing Sheets

(56) References Cited

OTHER PUBLICATIONS

Douglas C. Watson, et al., "Protection of Mice against *Salmonella typhimurium* with an O-Specific Polysaccharide-Protein Conjugate Vaccine" Infection and Immunity, vol. 60, No. 11, Nov. 1992, pp. 4679-4686.
Sarah A. Ngugi, et al., "Lipopolysaccharide from *Burkholderia thailandensis* E264 provides protection in a murine model of melioidosis" Vaccine, vol. 28, 2010, pp. 7551-7555.
Ken-ichi Tanamoto, "Endotoxin and the Quality Control of Medicine" Bull. Natl. Inst. Health Sci., vol. 126, 2008, pp. 19-33 (with partial English translation).
English translation of the International Preliminary Report on Patentability dated Oct. 9, 2014 in PCT/JP2013/054038.
Svenson et al 1981 (Infection and Immunity, May 1981, p. 490-496.
Combined Chinese Office Action and Search Report dated May 11, 2015 in Patent Application No. 201380015455.4 (with English language translation).
Office Action as received in the corresponding Chinese Patent Application No. 201380015455.4 dated Jan. 13, 2016 w/English Translation.
Extended Search Report dated Oct. 13, 2015 in European Patent Application No. 13763687.4.
Jorbeck et al 1981, Infection and Immunity, 32: p. 497-502.
Office Action dated Jul. 26, 2016 in Chinese Patent Application No. 201380015455.4 (with English translation).
Office Action dated Jul. 26, 2016 in European Patent Application No. 13 763 687.4
Combined Russian Office Action and Search Report dated Dec. 21, 2016 in Russian Patent Application No. 2014138021 (with English language translation).
Summons to attend oral proceedings pursuant to Rule 115(1) EPC dated Mar. 3, 2017 in European Patent Application No. 13763687.4.
Office Action dated Feb. 21, 2017 in Russian Patent Application No. 2014138021 (with English language translation).
Morbidity and Mortality Weekly Report (MMWR) from CDC Mar. 12, 2010 / 59(09):258-261.

\* cited by examiner

Fig. 1

| Vaccines | Amount of LPS EU/mL | Phenol extraction | Weeks after administration of vaccine | | | | | | In total (2-10 W) |
|---|---|---|---|---|---|---|---|---|---|
| | | | 2 | 3 | 4 | 6 | 8 | 10 | |
| Trivalent mixed whole-cells vaccine | 54,000 | — | 0.4 | 1.1 | 0.7 | 0.4 | 0.1 | 0 | 2.7 |
| Trivalent LPS vaccine | 54,000 | — | 0.5 | 0.7 | 0.5 | 0.2 | 0 | 0 | 1.9 |
| | 54,000 | + | 0 | 0.3 | 0.2 | 0 | 0 | 0 | 0.5 |
| | 5,400 | — | 0.1 | 0.3 | 0.2 | 0.2 | 0 | 0 | 0.8 |
| 10-valent mixed LPS vaccine | 7,200 | — | 0.4 | 0.9 | 0.7 | 0.2 | 0.1 | 0 | 2.3 |
| | 7,200 | + | 0 | 0.4 | 0.4 | 0 | 0 | 0 | 0.8 |
| OILVAX 7 | - | — | 0 | 0 | 0 | 0.2 | 0 | 0 | 0.2 |
| No vaccine | - | — | 0 | 0 | 0 | 0 | 0 | 0 | 0 |

LPS VACCINE

This application is a continuation of U.S. application Ser. No. 15/098,563 filed Apr. 14, 2016, which is and is a divisional of U.S. application Ser. No. 14/385,606 filed Sep. 16, 2014, now U.S. Pat. No. 9,345,756, and incorporated herein by reference, which is a National Stage application of PCT/JP2013/054038 filed Feb. 19, 2013 and claims the benefit of JP 2012-065162 filed Mar. 22, 2012.

TECHNICAL FIELD

The present invention provides a novel vaccine useful for preventing infectious diseases caused by Gram-negative bacteria such as *Salmonella* and *E. coli*. Specifically, the present invention relates to a method of immunizing non-human animals, in particular, birds using as a protective antigen a structure containing O-antigen (e.g. lipopolysaccharide) derived from Gram-negative bacteria.

BACKGROUND ART

Bacteria have different dye affinity depending upon different compositions of the cell wall when tested with Gram staining and are divided into two major groups of Gram-negative and Gram-positive bacteria based on differences in their dye affinity. In case of Gram-negative bacteria, the cell wall consists of an outer membrane and a peptidoglycan layer on the inside of the outer membrane. The outer membrane consists of phospholipids, lipopolysaccharides (LPS), lipoproteins and membrane proteins. A unit membrane structure of the outer membrane consists of phospholipids and lipopolysaccharides. A lipopolysaccharide is found in an outer layer of the membrane and a phospholipid in an inner layer thereof. A lipopolysaccharide consists of a high molecular weight lipid, called Lipid A, and a polysaccharide bound thereto. Lipid A makes up an outer layer of the outer membrane whereas a polysaccharide extends outwards from the outer membrane. The kind of saccharides is different from each other between the outer portion and the portion at the vicinity of Lipid A. The outer portion is called an O-side chain polysaccharide (O-antigen) and the inner portion is called a core polysaccharide. The saccharide consisting of O-antigen is chiefly a hexose and a pentose and a basic structure consisting of 3 to 5 kinds of these saccharides appear repeatedly. In the core polysaccharide are present, in addition to these saccharides, saccharides unique to the respective bacteria such as an octose, e.g. ketodeoxyoctonate, and a heptose. Lipid A is a lipid unique to the respective bacteria which comprises a saccharide, i.e. two molecules of glucosamine which are β-1,6-bound to each other, and phosphoric acid and a fatty acid bound to said saccharide. Lipid A is bound to a core polysaccharide at 6'-position of the saccharide.

There are many kinds of Gram-negative bacteria. *Salmonella* and *E. coli*, belonging to *Enterobacteriaceae*, and *Haemophilus*, belonging to *Pasteurella*, are also included in Gram-negative bacteria.

*Salmonella*, secondary large bacillus with peritrichous flagella, is divided into groups by the type of O-antigen and is further subdivided by the types of H-antigen, resulting in more than 2,000 kinds of serotype. A host range of *Salmonella* is quite wide and a variety of mammals including human and birds are known to be infected with or to hold *Salmonella*. When chicken are infected, *Salmonella* may cause septic diseases in young chicks. In case of adult chickens, however, carrier chickens are asymptomatic to escape culling and as a result chicken meat and eggs derived from chickens contaminated with *Salmonella* are distributed to induce food poisoning in human through food products manufactured thereby.

Food poisoning by *Salmonella* develops after a latent period of 12 to 48 hours after intake of contaminated food. A latent period may vary depending on an intake amount of bacteria, the condition and age of patients. Symptoms are mainly acute gastroenteritis and cardinal symptoms are diarrhea, abdominal pain, vomiting and fever. Thus, a *salmonella* vaccine for chicken is not preventing chickens from the disease onset but is an important vaccine used for public health.

Among conventional vaccines against *Salmonella* is a whole-cells vaccine which comprises cells of inactivated *Salmonella*. A whole-cells vaccine, however, may cause side effects since it contains portions that are not of antigenicity. In case of chickens that are bred in flocks, in view of labor saving of vaccination, there is a strong demand for a multivalent vaccine that may prevent many diseases with a single injection. Also, a multivalent vaccine may contribute to reduction of stress in chickens since it reduces the number of injections. However, although a multivalent vaccine has such convenience, it is liable to cause vaccination reaction at the injection site, in particular, when it contains bacteria such as *Salmonella*.

Under the circumstances, research of a component vaccine against *Salmonella* has been conducted, among which application of a lipopolysaccharide (O-antigen) is studied. For instance, there is a report that a conjugate consisting of O-antigen derived from *Salmonella Typhimurium* bound to a carrier protein is administered to mice to confirm its efficacy (Non-patent reference 1). There is also a report that a lipopolysaccharide derived from *Salmonella Typhi* is administered to mice to confirm its efficacy (Patent reference 1). Other than *Salmonella*, there is a report that a lipopolysaccharide derived from *Burkholderia thailandensis* or *Burkholderia pseudomallei* is administered to mice to confirm its efficacy (Patent reference 2, Non-patent reference 2).

However, contamination of a lipopolysaccharide is avoided with meticulous care in a medicament used for living body since a lipopolysaccharide may clinically cause a variety of highly lethal diseases such as septic shock, disseminated intravascular coagulation (DIC) and multiple organ failure (MOF) and may become a causal factor of fever even in a trace amount (Non-patent reference 3). In practice, it is reported that more than 90% of mice die within 72 hours when administered with a lipopolysaccharide (Patent reference 3). Under the circumstances, an idea to use a lipopolysaccharide per se as a vaccine antigen would not arise generally.

PATENT REFERENCES

Patent reference 1: WO2004/052394
Patent reference 2: WO2010/082020
Patent reference 3: Japanese Patent Publication No. 2001-26602

NON-PATENT REFERENCES

Non-patent reference 1: Infect. Immun, 60, pp 4679-4686, 1992
Non-patent reference 2: Vaccine, 28, pp 7551-7555, 2010
Non-patent reference 3: Bull. Natl. Inst. Health Sci., 126, pp 19-33, 2008

Non-patent reference 4: AVIAN DISEASES, 53, pp 281-286, 2009

DISCLOSURE OF THE INVENTION (Technical Problem to be Solved by the Invention)

The present invention aims at making it possible to produce a multivalent vaccine and a mixed vaccine for a vaccine against Gram-negative bacteria such as *Salmonella* and *E. coli* and at reducing inoculation reaction.

(Means for Solving the Problems)

The present inventors have earnestly studied the problems mentioned above and as a result have found that swelling at the injection site is unexpectedly restrained when a vaccine comprising as an active ingredient a structure containing O-antigen (e.g. lipopolysaccharide) derived from Gram-negative bacteria is administered to birds. Namely, a structure containing O-antigen is released from cells contained in culture of Gram-negative bacteria (e.g. *Salmonella*), e.g. by sonication or phenol treatment, and then is collected with a column to which said structure is adhered to. A vaccine composition comprising as an active ingredient the aforementioned structure is then prepared via a step of emulsification, if necessary. The present inventors have found that the thus prepared vaccine composition may confer immunization against said Gram-negative bacteria to birds (e.g. chicken) when immunized therewith with no specific side effects to thereby complete the present invention.

The present invention includes the following inventions.

[1] A vaccine composition for birds comprising as an active ingredient a structure containing O-antigen derived from Gram-negative bacteria, provided that said structure does not contain a whole cell.

[2] The vaccine composition according to [1] wherein the structure containing O-antigen is lipopolysaccharide.

[3] The vaccine composition according to [1] or [2] wherein Gram-negative bacteria are *Enterobacteriaceae* or *Pasteurella*.

[4] The vaccine composition according to [3] wherein *Enterobacteriaceae* is *Salmonella* or *E. coli*.

[5] The vaccine composition according to [4] wherein *Salmonella* is one or more selected from the group consisting of O4, O7 and O9 Groups.

[6] The vaccine composition according to [4] or [5] wherein *Salmonella* is one or more selected from the group consisting of *Salmonella Enteritidis*, *Salmonella Typhimurium* and *Salmonella Infantis*.

[7] The vaccine composition, according to [4] or [5] wherein the structure containing O-antigen derived from Gram-negative bacteria is a mixture of structures containing O-antigen derived from *Salmonella Enteritidis*, *Salmonella Typhimurium* and *Salmonella Infantis*.

[8] The vaccine composition according to [4] wherein *E. coli* is *E. coli* having O-antigen of O78.

The vaccine composition according to [3] wherein *Pasteurella* is *Haemophilus*.

[10] The vaccine composition according to [9] wherein *Haemophilus* is *Haemophilus paragallinarum*.

[11] The vaccine composition according to any one of [1] to [10] wherein the structure containing O-antigen is a structure containing O-antigen contained at at least 5,400 EU/ml from each *Salmonella* in the vaccine composition.

[12] The vaccine composition according to any one of [1] to [11] wherein the vaccine composition further comprises an antigen derived from one or more pathogens selected from the group consisting of Newcastle disease virus, avian infectious bronchitis virus, *Mycoplasma gallisepticum*, Egg drop syndrome virus and *Haemophilus paragallinarum*.

[13] A process for preparing a vaccine composition for birds comprising as an active ingredient a structure containing O-antigen derived from Gram-negative bacteria, the process comprising the steps (1) to (4) as follows:

(1) a step of culturing Gram-negative bacteria (step of culture);

(2) a step of releasing the aforementioned structure from cells contained in the solution after said culture (step of release);

(3) a step of collecting the aforementioned structure from the solution after said release (step of collection); and (4) a step of preparing the solution after said collection to obtain a vaccine composition (step of preparation).

[14] The process according to [13] wherein the step of releasing the aforementioned structure is a step of sonication or a step of treatment with phenol.

[15] The process according to [13] or [14] wherein the process further comprises a step of inactivating cells (step of inactivation) and/or a step of emulsifying the aforementioned structure (step of emulsification).

[16] The process according to [15] wherein the step of inactivation is carried out after the step of culture and the step of emulsification is carried out after the step of collection.

[17] The process according to any one of [13] to [16] wherein the process further comprises a step of measuring an amount of the aforementioned structure (step of measurement).

[18] The process according to [17] wherein the step of measurement is carried out after the step of collection.

[19] The process according to any one of [13] to [18] wherein the process further comprises a step of removing Lipid A (step of removing Lipid A).

[20] The process according to [19] wherein the step of removing Lipid A is carried out after the step of collection.

EFFECTS OF THE INVENTION

By using a structure containing O-antigen (e.g. lipopolysaccharide) derived from Gram-negative bacteria as an active ingredient of a vaccine composition, it becomes possible to alleviate swelling at the injection site as compared to the conventional whole-cells vaccine. Besides, by preparing a component vaccine, it becomes possible to further increase the number of other antigens to be mixed therewith without increasing an amount of injection.

BRIEF DESCRIPTION OF DRAWINGS

FIG. 1 shows a swelling score at the injection site for a mixed vaccine of lipopolysaccharides derived from *Salmonella Enteritidis*, *Salmonella Infantis* and *Salmonella Typhimurium* (trivalent LPS vaccine) or a vaccine comprising other antigens in addition to the trivalent LPS vaccine (10-valent mixed LPS vaccine).

BEST MODE FOR CARRYING OUT THE INVENTION

1. Vaccine Composition

Figure 2:
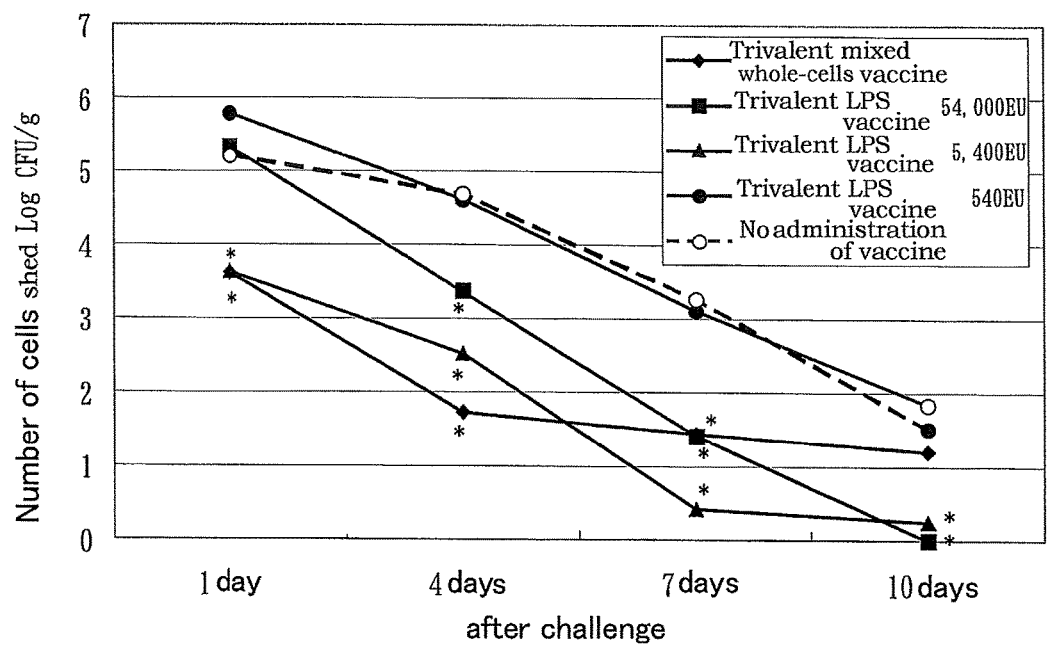
FIG. 2 shows the number of cells shed when a challenge test with *Salmonella Typhimurium* is carried out for trivalent LPS vaccine wherein the asterisk * shows a significant difference from control group ($p<0.05$).

The first embodiment of the present invention is a vaccine composition for birds comprising as an active ingredient a structure containing O-antigen derived from Gram-negative bacteria.

In accordance with the present invention, in a vaccine composition comprising as an active ingredient a structure containing O-antigen (specifically, lipopolysaccharide) derived from *Salmonella Typhimurium*, *Salmonella Infantis* or *Salmonella Enteritidis*, the shedding of cells is reduced against challenge with the respective cells. It is assumed to be due to maintenance of antigenicity against the respective structures derived from a plurality of Gram-negative bacteria even if the respective structures are mixed together. Besides, in the 10-valent mixed vaccine comprising the trivalent vaccine mixed with antigens different from the aforementioned structures, antigenicity against cells that provided the aforementioned structures is maintained. It is assumed to be due to maintenance of antigenicity against the aforementioned structures even if the mixed vaccine comprises antigens other than the aforementioned structures.

As such, the vaccine composition of the present invention includes:

(A) a vaccine composition comprising as an active ingredient the aforementioned structure derived from a single Gram-negative bacteria (hereinafter also referred to as "monovalent vaccine");

(B) a vaccine composition comprising as an active ingredient the aforementioned structure derived from a plurality of Gram-negative bacteria (hereinafter also referred to as "polyvalent vaccine"); and (C) a vaccine composition comprising a monovalent vaccine or a polyvalent vaccine together with antigens different from the aforementioned structure (hereinafter also referred to as "mixed vaccine").

(1) Bacterial Cells

The vaccine composition of the present invention comprises as an active ingredient a structure containing O-antigen. Thus, the vaccine composition of the present invention may widely be applied to Gram-negative bacteria having the aforementioned structure. For instance, Gram-negative bacteria as used in the present invention may include Gram-negative facultatively anaerobic rod, *Anaplasmataceae*, *Arcobacter*, *Bartonellaceae*, *Brachyspira*, *Buchnera*, *Campylobacter*, *Chlamydiales*, *Chloroflexus*, Gram-negative aerobic bacteria, Gram-negative anaerobic bacteria, Gram-negative oxygenic photosynthetic bacteria, *Helicobacter*, Lawsonia bacteria, *Methylosinus*, *Oceanospirillaceae*, *Ornithobacterium*, *Piscirickettsiaceae*, *Rhodobacter*, *Rhodomicrobium*, *Rhodovulum*, *Rickettsiaceae*, *Roseobacter*, *Spirillaceae*, and *Tenericutes*, preferably Gram-negative facultatively anaerobic rod.

Gram-negative facultatively anaerobic rod may include *Enterobacteriaceae*, *Pasteurellaceae*, *Actinobacillus*, *Aeromonadaceae*, *Azoarcus*, *Capnocytophaga*, *Cardiobacteriaceae*, *Chromobacterium*, *Eikenella*, *Gardnerella*, *Moritella*, *Rahnella*, *Shewanella*, *Streptobacillus*, *Vibrionaceae*, and *Zymomonas*, preferably *Enterobacteriaceae* and *Pasteurellaceae*.

*Enterobacteriaceae* may include *Salmonella*, *Escherichia*, *Calymmatobacterium*, *Citrobacter*, *Edwardsiella*, *Enterobacter*, *Erwinia*, *Hafnia*, *Klebsiella*, *Kluyvera*, *Morganella*, *Pantoea*, *Pectobacterium*, *Photorhabdus*, *Plesiomonas*, *Proteus*, *Providencia*, *Serratia*, *Shigella*, *Wigglesworthia*, *Xenorhabdus*, and *Yersinia*, preferably *Salmonella* and *Escherichia*.

*Salmonella* is divided into groups by the types of O-antigen and is further subdivided by the types of H-antigen, including O2 Group (A), O4 Group (B), O7 Group (C1, C4), O8 Group (C2, C3), O9 Group (D1), and O3/O10 Group (E1, E2, E3) as shown in Table 1 and Table 2 (the old designation shown in the parenthesis).

TABLE 1

| O-Serotype | Serotype | O-Antigen: (optionally deleted) |
|---|---|---|
| O2 (A) | *Salmonella Paratyphi* A | 1, 2, 12 |
| O4 (B) | *Salmonella Paratyphi* B | 1, 4, (5), 12 |
| | *Salmonella Stanley* | 1, 4, (5), 12, 27 |
| | *Salmonella Derby* | 1, 4, (5), 12 |
| | *Salmonella Agona* | 1, 4, 12 |
| | *Salmonella Typhimurium* | 1, 4, (5), 12 |
| | *Salmonella Heidelberg* | 1, 4, (5), 12 |
| O7 (C1, C4) | *Salmonella Paratyphi* C | 6, 7, (Vi) |
| | *Salmonella Choleraesuis* | 6, 7, |
| | *Salmonella Braenderup* | 6, 7, 14 |
| | *Salmonella Montevideo* | 6, 7, 14 |
| | *Salmonella Thompson* | 6, 7, 14 |
| | *Salmonella Virchow* | 6, 7 |
| | *Salmonella Infantis* | 6, 7, 14 |
| | *Salmonella Bareilly* | 6, 7, 14 |
| | *Salmonella Tennessee* | 6, 7, 14 |

TABLE 2

| O-Serotype | Serotype | O-Antigen: (optionally deleted) |
|---|---|---|
| O8 (C2, C3) | *Salmonella Narashino* | 6, 8 |
| | *Salmonella Newport* | 6, 8, 20 |
| | *Salmonella Lichfield* | 6, 8 |
| O9 (D1) | *Salmonella Sendai* | 1, 9, 12 |
| | *Salmonella Typhi* | 9, 12, (Vi) |
| | *Salmonella Enteritidis* | 1, 9, 12 |
| | *Salmonella Panama* | 1, 9, 12 |
| | *Salmonella enterica* subsp. *salamae* | 1, 9, 12 |
| | *Salmonella Gallinarum* | 1, 9, 12 |
| O3/O10 (E1, E2, E3) | *Salmonella Anatum* | 3, 10, (15), (15, 34) |
| | *Salmonella Meleagridis* | 3, 10, (15), (15, 34) |
| | *Salmonella London* | 3, 10, (15) |
| | *Salmonella Give* | 3, 10, (15), (15, 34) |
| | *Salmonella Weltevreden* | 3, 10, (15) |

In accordance with the present invention, in a trivalent vaccine comprising as an active ingredient a structure containing O-antigens derived from *Salmonella Typhimurium* (O4 Group), *Salmonella Infantis* (O7 Group) and *Salmonella Enteritidis* (O9 Group), the shedding of cells is reduced against challenge with the respective cells. It is assumed to be due to maintenance of antigenicity of the aforementioned structures prepared by the process for preparation of the present invention irrespective of the types of O-antigen. Thus, it is assumed that the vaccine composition of the present invention may be applicable to *Salmonella* as whole but not limited to *Salmonella* belonging to O4 Group, O7 Group and O9 Group.

In Non-Patent Reference 4, in birds immunized with a vaccine comprising cells of *Salmonella Typhimurium*, *Salmonella Infantis* and *Salmonella Enteritidis*, the shedding of cells is reduced against challenge not only with the respective vaccine strains but also with *Salmonella Heidelberg* belonging to the same O-antigen group (O4 Group) as *Salmonella Typhimurium*. Thus, it is assumed that the vaccine may also be effective for cells that have homologous O-antigen to that of the vaccine strains but are of different serotypes. Namely, in case of a *Salmonella* vaccine, it is assumed that the vaccine may also be effective for cells having homologous O-antigen to that of the vaccine strains, in other words, for cells of the same O-antigen Group as that of the vaccine strains. Therefore, the vaccine composition of the present invention, when applied for *Salmonella*, may also be applicable to the other *Salmonella* cells belonging to O4 Group, O7 Group and O9 Group.

Thus, the vaccine composition of the present invention includes:
(A) a monovalent vaccine comprising as an active ingredient a structure containing O-antigen derived from *Salmonella*;
(B) a polyvalent vaccine comprising as an active ingredient structures containing O-antigen derived from two or more *Salmonella*;
(C) a monovalent vaccine comprising as an active ingredient a structure containing O-antigen derived from *Salmonella* belonging to O4 Group, O7 Group or O9 Group;
(D) a polyvalent vaccine comprising as an active ingredient structures containing O-antigen derived from two or more *Salmonella* selected from the group consisting of O4 Group, O7 Group and O9 Group; and
(E) a mixed vaccine comprising the above monovalent vaccine or the polyvalent vaccine together with antigens different from the aforementioned structure.

Exemplary *Salmonella* included in *Salmonella*, O4 Group, O7 Group or O9 Group may include the cells shown in Table 1 and Table 2. Preferably, *Salmonella* is those belonging to O4 Group, Group and O9 Group. Also, preferably, O4 Group is *Salmonella Typhimurium*, O7 Group is *Salmonella Infantis* and O9 Group is *Salmonella* Enteritidis.

*E. coli* is classified by a combination of three antigens, O-antigen, K-antigen and H-antigen. About 160 types for O-antigen, about 100 types for K-antigen and about 56 types for H-antigen are known. Specific types of *E. coli* may develop diarrhea and gastroenteritis and may be a cause of food poisoning. Such *E. coli* is generally classified into enterotoxigenic *E. coli*, enteroinvasive *E. coli*, enterohaemorrhagic *E. coli*, enteropathogenic *E. coli*, enterotoaggregative *E. coli* and diffusely adherent *E. coli*. Groups belonging to enterotoxigenic *E. coli* include O18, O26, O44, O55, O86, O111, O112, O114, O119, O125, O126, O127, O128a, and O142. Enterotoxigenic *E. coli* includes O4, O6, O7, O8, O9, O15, O18, O20, O25, O27, O63, O77, O78, O80, O85, O114, O115, O126, O128a, O139, O148, O153, O159, O167, O168, and O169. Enteroinvasive *E. coli* includes O28c, O29, O112a, O124, O136, O143, O144, O152, O164, and O167. Enterohaemorrhagic *E. coli* includes O1018, O26, O91, O111, O113, O114, O115, O117, O119, 0121, O128, O145, and O157. Such *E. coli* is preferably O78.

*Pasteurellaceae* includes *Haemophilus*, *Mannheimia* and *Pasteurella*, preferably *Haemophilus*.

*Haemophilus* includes *Haemophilus paragallinarum*, *Haemophilus ducreyi*, *Haemophilus influenzae*, *Haemophilus parainfluenzae*, *Haemophilus paraphrophilus*, *Haemophilus parasuis*, and *Haemophilus somnus*, preferably *Haemophilus paragallinarum*.

(2) Structure Containing O-Antigen

The vaccine composition of the present invention comprises as an active ingredient a structure containing O-antigen. Since O-antigen is mainly responsible for antigenicity, a structure containing O-antigen may be any structure as far as it contains O-antigen provided that it is a structure that does not contain a whole cell. For instance, a structure containing O-antigen includes lipopolysaccharides and a structure containing lipopolysaccharides from which Lipid A is excluded (e.g. a structure consisting of O-antigen or O-antigen and a core polysaccharide). In case that a step of removing Lipid A is not used for the purpose of efficient production, the vaccine composition of the present invention preferably comprises as an active ingredient lipopolysaccharides. Although there is no concern about side effects for the vaccine composition of the present invention, the vaccine composition of the present invention preferably comprises as an active ingredient a structure containing lipopolysaccharides from which Lipid A is excluded for higher safety.

(3) Monovalent Vaccine

The vaccine composition of the present invention includes a vaccine composition comprising as an active ingredient the aforementioned structure derived from a single kind of Gram-negative bacteria (monovalent vaccine).

In case of a monovalent vaccine, Gram-negative bacteria may suitably be selected from the cells of Gram-negative bacteria as described above. Gram-negative bacteria are preferably *Enterobacteriaceae* or *Pasteurella*. *Enterobacteriaceae* is preferably *Salmonella* or *E. coli*. *Salmonella* is preferably *Salmonella* belonging to O4, O7 and O9 Groups. *Salmonella* belonging to O4 Group is preferably *Salmonella Typhimurium*, *Salmonella* belonging to O7 Group is preferably *Salmonella Infantis*, and *Salmonella* belonging to O9 Group is preferably *Salmonella Enteritidis*. *E. coli* is preferably *E. coli* having O-antigen of O78. *Pasteurella* is preferably *Haemophilus*, in particular, *Haemophilus paragallinarum*.

Thus, a monovalent vaccine of the present invention includes:
(A) a vaccine composition comprising as an active ingredient O-antigen derived from a single kind of Gram-negative bacteria;
(B) a vaccine composition comprising as an active ingredient O-antigen derived from a single kind of *Enterobacteriaceae*;
(C) a vaccine composition comprising as an active ingredient O-antigen derived from a single kind of *Pasteurella*;
(D) a vaccine composition comprising as an active ingredient O-antigen derived from a single kind of *Salmonella*;
(E) a vaccine composition comprising as an active ingredient O-antigen derived from a single kind of *E. coli*;
(F) a vaccine composition comprising as an active ingredient O-antigen derived from a single kind of *Salmonella* belonging to O4 Group;
(G) a vaccine composition comprising as an active ingredient O-antigen derived from a single kind of *Salmonella* belonging to O7 Group;

(H) a vaccine composition comprising as an active ingredient O-antigen derived from a single kind of *Salmonella* belonging to O9 Group;
(I) a vaccine composition comprising as an active ingredient O-antigen derived from *Salmonella Typhimurium*;
(J) a vaccine composition comprising as an active ingredient O-antigen derived from *Salmonella Infantis*;
(K) a vaccine composition comprising as an active ingredient O-antigen derived from *Salmonella Enteritidis*;
(L) a vaccine composition comprising as an active ingredient O-antigen derived from a single kind of *E. coli* having O-antigen of O78;
(M) a vaccine composition comprising as an active ingredient O-antigen derived from a single kind of *Haemophilus*; and
(N) a vaccine composition comprising as an active ingredient O-antigen derived from *Haemophilus paragallinarum*.

(4) Polyvalent Vaccine

The vaccine composition of the present invention includes a vaccine composition comprising as an active ingredient the aforementioned structure derived from plural kinds of Gram-negative bacteria (polyvalent vaccine).

In case of a polyvalent vaccine, the kind of Gram-negative bacteria from which a structure containing O-antigen is derived is preferably 2 or more, 3 or more, 4 or more, or 5 or more. It is preferably 2 (bivalent vaccine), 3 (trivalent vaccine), 4 (4-valent vaccine), or 5 (5-valent vaccine).

A trivalent vaccine of *Salmonella* preferably comprises the aforementioned structures derived from *Salmonella Typhimurium*, *Salmonella Infantis* and *Salmonella Enteritidis*.

Gram-negative bacteria may suitably be selected from the cells of Gram-negative bacteria as described above. Gram-negative bacteria are preferably *Enterobacteriaceae* or *Pasteurella*. *Enterobacteriaceae* is preferably *Salmonella* or *E. coli*. *Salmonella* is preferably *Salmonella* belonging to O4, O7 and O9 Groups. *Salmonella* belonging to O4 Group is preferably *Salmonella Typhimurium*, *Salmonella* belonging to O7 Group is preferably *Salmonella Infantis*, and *Salmonella* belonging to O9 Group is preferably *Salmonella Enteritidis*. *E. coli* is preferably *E. coli* having O-antigen of O78. *Pasteurella* is preferably *Haemophilus*, in particular, *Haemophilus paragallinarum*.

Thus, a polyvalent vaccine of the present invention includes:
(A) a vaccine composition comprising as an active ingredient O-antigens derived from two or more kinds of Gram-negative bacteria;
(B) a vaccine composition comprising as an active ingredient O-antigens derived from two or more kinds of *Enterobacteriaceae*;
(C) a vaccine composition comprising as an active ingredient O-antigens derived from two or more kinds of *Pasteurella*;
(D) a vaccine composition comprising as an active ingredient O-antigens derived from two or more kinds of *Salmonella*;
(E) a vaccine composition comprising as an active ingredient O-antigens derived from two or more kinds of *E. coli*;
(F) a vaccine composition comprising as an active ingredient O-antigens derived from *Salmonella* belonging to O4 Group and *Salmonella* belonging to O7 Group;
(G) a vaccine composition comprising as an active ingredient O-antigens derived from *Salmonella* belonging to O4 Group and *Salmonella* belonging to O9 Group;
(H) a vaccine composition comprising as an active ingredient O-antigens derived from *Salmonella* belonging to O7 Group and *Salmonella* belonging to O9 Group;
(I) a vaccine composition comprising as an active ingredient O-antigens derived from *Salmonella* belonging to O4 Group, *Salmonella* belonging to O7 Group and *Salmonella* belonging to O9 Group;
(J) a vaccine composition comprising as an active ingredient O-antigens derived from *Salmonella Typhimurium* and *Salmonella Infantis*;
(K) a vaccine composition comprising as an active ingredient O-antigens derived from *Salmonella Typhimurium* and *Salmonella Enteritidis*;
(L) a vaccine composition comprising as an active ingredient O-antigens derived from *Salmonella Infantis* and *Salmonella Enteritidis*;
(M) a vaccine composition comprising as an active ingredient O-antigens derived from *Salmonella Typhimurium*, *Salmonella Infantis* and *Salmonella Enteritidis*;
(N) a vaccine composition comprising as an active ingredient O-antigens derived from two or more kinds of *E. coli* having O-antigen of O78; and
(O) a vaccine composition comprising as an active ingredient O-antigens derived from two or more kinds of *Haemophilus*.

(5) Mixed Vaccine

The vaccine composition of the present invention includes a vaccine composition comprising a monovalent vaccine or a polyvalent vaccine together with antigens different from the aforementioned structure (mixed vaccine).

Such antigens include an attenuated pathogen, an inactivated pathogen, a protein, a peptide, a nucleic acid, and a virus-like particle. The monovalent vaccine or the polyvalent vaccine of the present invention may be used as a mixed vaccine in combination with at least one vaccine selected from the group consisting of vaccines against other viruses (e.g. infectious bronchitis virus, infectious bursal disease virus, avian encephalomyelitis virus, Egg drop syndrome virus, Newcastle disease virus, Avian reovirus, avian influenza virus, Marek's disease virus, infectious laryngotracheitis virus, avian pneumovirus, and fowlpox virus), bacteria (e.g. *Mycoplasma gallisepticum*, *Mycoplasma synoviae*, *Clostridium septicum*, *Clostridium perfringens*, *Campylobacter jejuni*, and *Campylobacter fetus*) and protozoa (e.g. *Leucocytozoon caulleryi*, *Eimeria tenella*, *Eimeria maxima*, and *Eimeria necatrix*).

(6) Concentration and Ratio of Active Ingredient

The vaccine composition of the present invention comprises as an active ingredient a structure containing O-antigen. A concentration of the aforementioned structure is determined using endotoxin unit (=EU) as an index. EU is measured pursuant to 2-(6) step of measurement as described below. A concentration of the aforementioned structure contained in a vaccine composition, in case of a polyvalent vaccine, may vary dependent upon the kind of the aforementioned structure or may be the same. A concentration of the aforementioned structure is preferably at least 5,400 EU/mL, and more preferably 54,000 EU/mL, for the respective structure.

In case of a polyvalent vaccine, a ratio of the aforementioned structure (EU ratio) may be either equal or different ratio. In case of a trivalent vaccine comprising as an active ingredient the aforementioned structure derived from *Salmonella Typhimurium*, *Salmonella Infantis*, or *Salmonella Enteritidis*, a ratio of the aforementioned structure is preferably *Salmonella Typhimurium*: *Salmonella Infantis*: *almonella Enteritidis* (1:1:1).

(7) Subject for Administration

In accordance with the present invention, the shedding of cells into the cecal droppings in chickens immunized with a trivalent vaccine was reduced as in Example 1. Thus, the vaccine composition of the present invention may be used for birds. Birds include ones bred for commercial and non-commercial purpose. Examples of birds include *Galliformes* (e.g. chicken, quails, and turkey), *Anseriformes* (e.g. duck, and goose), *Charadriiformes* (e.g. gull, barred button quail, and plover), *Columbiformes* (e.g. pigeon), *Struthioniformes* (e.g. ostrich), *Passeriformes* (e.g. crow, finch, sparrow, starling, and swallow), *Psittaciformes* (e.g. parrot), *Falconiformes* (e.g. eagle, and falcon), *Strigiformes* (e.g. owl), *Sphenisciformes* (e.g. penguin), and *Psittaciformes* (e.g. parakeet, and parrot), preferably chicken.

(8) Route of Administration

The vaccine composition of the present invention has swelling at the site of administration restrained to a level acceptable as a vaccine. Thus, a variety of routes of administration may be conceived for the vaccine composition of the present invention, including e.g. the leg, the breast, cervix, oral, rectal, percutaneous, enteric administration, intramuscular, subcutaneous, intramedullary injection, direct intraventricular, intravenous, intraperitoneal, intranasal and intraocular injection. The leg is a convenient administration route of a vaccine composition. Thus, a preferable route of administration is the leg.

(9) Carrier

The vaccine composition of the present invention may comprise a pharmaceutically acceptable carrier. For a pharmaceutically acceptable carrier, any carrier used for production of a vaccine may be used without limitation. Specifically, a carrier includes saline, buffered saline, dextrose, water, glycerol, isotonic aqueous buffer and a combination thereof. In addition to this, the vaccine composition of the present invention may further comprise an emulsifying agent, a preserving agent (e.g. thimerosal), an isotonic agent, a pH adjuster, an inactivating agent (e.g. formalin), and an adjuvant. An adjuvant is preferably oil adjuvant.

(10) Carrier Protein

A structure containing O-antigen may optionally be bound to a carrier protein for the purpose of enhancing an immunization reaction when administered. Such a carrier protein includes diphtheria toxoid (DT), tetanus toxoid (TT), cholera toxin (CT) and CRM197. Binding to a carrier protein may be done via a linker (e.g. SPDP or ADH) or the structure may directly be bound to a carrier protein. As an example, binding to a carrier protein (DT/TT/CT) via SPDP or ADH using cyanogen bromide is disclosed (Non-patent reference 1).

2. Process for Preparing Vaccine Composition

The second embodiment of the present invention is a process for preparing a vaccine composition for birds comprising as an active ingredient a structure containing O-antigen derived from Gram-negative bacteria.

The process of the present invention comprises a step of culturing Gram-negative bacteria (step of culture); a step of releasing the aforementioned structure from cells contained in the solution after said culture (step of release); a step of collecting the aforementioned structure from the solution after said release (step of collection), and a step of preparing the solution after said collection to obtain a vaccine composition (step of preparation). In addition to the above steps, the process may further comprise a step of inactivating cells (step of inactivation) and/or a step of emulsifying the aforementioned structure (step of emulsification). Preferably, the step of inactivation is carried out after the step of culture and the step of emulsification is carried out after the step of collection. Besides, the process preferably comprises a step of measuring an amount of the aforementioned structure (step of measurement) after the step of collection. In case that the aforementioned structure is one that does not contain Lipid A, the process preferably comprises a step of removing Lipid A (step of removing Lipid A). The step of removing Lipid A is preferably carried out after the step of collection.

Each of the respective steps is explained below. As occasion demands, the respective steps are not necessarily carried out in the order indicated below, some steps may be omitted, or some steps may be carried out repeatedly. For instance, the step of emulsification needs not be carried out when oil adjuvant is not used. The step of inactivation and the step of release may be carried out simultaneously (e.g. sonication and formalin treatment are done in both steps).

(1) Step of Culture

The step of culture may suitably be modified for the kind of culture medium and growth condition (time, temperature, oxygen concentration, carbon dioxide concentration, pH, and salt concentration) depending on the kind of Gram-negative bacteria. In case of *Salmonella*, the cells are cultured on TPB culture at 35° to 43° C. (preferably at 37° C.) for 8 to 24 hours (preferably 16 hours). In case of *E. coli*, the cells are cultured on LB culture at 30° C. to 43° C. (preferably at 37° C.) for 8 to 24 hours (preferably 16 hours).

(2) Step of Inactivation

The step of inactivation may suitably be modified depending on the kind of Gram-negative bacteria. For instance, it may be done with physical treatment (e.g. X ray radiation, heat treatment, or sonication) or chemical treatment (e.g. formalin treatment, mercury treatment, alcohol treatment, or hydrogen treatment). Any of these treatments may be done alone or in combination thereof. Formalin treatment is preferable.

(3) Step of Release

The step of release may be any procedures providing antigenicity of the aforementioned structure is retained. The procedures and the conditions may suitably be selected depending upon Gram-negative bacteria or the property of the aforementioned structure. For instance, it includes sonication, phenol treatment, mechanical treatment, freezing and thawing, compression and decompression, osmotic pressure, cell wall decomposition (e.g. lysozyme treatment disclosed in Non-patent reference 1 and Non-patent reference 2), and surfactant treatment, either alone or in combination thereof, preferably cell wall decomposition, sonication, or phenol treatment.

Sonication may be conducted under any conditions providing antigenicity of the aforementioned structure is retained. For instance, it may be done at 25° C. or less, preferably in ice water, for 5 to 30 minutes, preferably for 15 minutes. The solution after sonication may be subject to centrifugation for removing impurities.

Phenol treatment may be conducted under any conditions providing antigenicity of the aforementioned structure is retained. For instance, it may be done with 45 to 100%, preferably 100%, phenol at 4 to 80° C., preferably at 68° C. for 5 to 30 minutes, preferably for 15 minutes. During the procedure, a container may be stirred at regular time intervals. The solution after the reaction may be subject to centrifugation for removing impurities. The solution after phenol treatment may be subject to dialysis with a suitable buffer (e.g. PBS).

Nucleolytic treatment (e.g. DNase treatment or RNase treatment) or proteolytic treatment (protease treatment) may be conducted after the step of release, as disclosed in Non-patent reference 1 and Non-patent reference 2. Nucleic acids may be removed by ethanol fractionation. Removal of proteins and removal of fatty acid side chain of Lipid A may be conducted by acetic acid treatment.

(4) Step of Collection

The step of collection may suitably be modified depending upon the property of the aforementioned structure. For instance, lipopolysaccharide is negatively charged as a whole as comprising a lot of phosphate groups and thus is easily adsorbed to a positively charged substance. Therefore, the aforementioned structure may be collected by adsorption utilizing such property such as affinity chromatography and adsorption with a positively charged membrane. For instance, Polymyxin B, histidine, histamine, lysine, aminated poly(γ-methyl-L-glutamic acid) beads, and a positively charged membrane with introduced ammonium groups may be conceived for a positively charged substance.

Alternatively, the aforementioned structure may be collected by utilizing hydrophobicity of Lipid A. A hydrophobic substance includes polypropylene, polyethylene, polystyrene, and PTEE membrane. For collecting the aforementioned structure, it is also conceived that a substance binding to lipopolysaccharide is utilized including an anti-LPS antibody, an anti-LPS factor from *Limulus polyphemus*, BPI (bactericidal permeability increasing) protein, CAP18 (cationic antibacterial protein of 18 kDa), and LBP (LPS-Binding-Protein). Chromatography with a carrier to which such a substance is bound may be used.

Collection of the aforementioned structure may be attained by using commercially available products. For instance, ET-clean (registered trademark; Chisso Corporation) may be used. Collection may also be done by ultracentrifugation as disclosed in Non-patent reference 1.

(5) Step of Removing Lipid A

A structure containing O-antigen may be one that contains Lipid A (e.g. lipopolysaccharide) or one that does not contain Lipid A (e.g. O-antigen, O-antigen plus core polysaccharide). In case of a structure that does not contain Lipid A, the step of removing Lipid A is preferably incorporated.

The step of removing Lipid A includes, as an example, heat treatment with addition of an acid. An exemplary process includes treatment with 1% acetic acid at 100° C. for 90 minutes (Non-patent reference 1). This process is combined with a process of isolating Lipid A as removed. An exemplary process for isolating Lipid A includes ultracentrifugation (Non-patent reference 1).

(6) Step of Measurement

An exemplary process for measuring lipopolysaccharide may be carried as described below. A solution of the aforementioned structures diluted with distilled water and reference standard of CSE-L set (*E. coli* O113: endotoxin derived from H10) are added to a microplate. LAL reagent of Endospecy ES-50M Set (SEIKAGAKU BIOBUSINESS CORPORATION) is added. The plate is covered for the reaction at 37° C. for 30 minutes. A mixture of sodium nitrite/hydrochloric acid, an ammonium sulphamate solution, and a mixture of N-(1-naphtyl)ethylenediamine dihydrochloride/N-methyl-2-pyrrolidone in Toxicolor System DIA Set (SEIKAGAKU BIOBUSINESS CORPORATION) are added and the microplate is well shaken. Absorbance is measured at two wavelengths 545 nm and 630 nm (Molecular Devices Japan, VersaMax) to determine endotoxin.

(7) Step of Emulsification

The step of emulsification is a process of mixing together a solution containing the aforementioned structure, oil and an emulsifying agent. An emulsifying agent includes Tween 80 (registered trademark), Tween 60 (registered trademark), Brij 721 (registered trademark), Eumulgin B2 (registered trademark), Arlacel 165 FL (registered trademark), Tefose 1500 (registered trademark), Glucamate SSE20 (registered trademark), Surf hope C-1216 (registered trademark), Surf hope C-1811 (registered trademark), Surhope SE Pharma D-1816 (registered trademark), Surf hope SE Pharma D-1616 (registered trademark), Span 60 (registered trademark), Olepal isostearique (registered trademark), Glucate SS (registered trademark), and Surf hope C-1205 (registered trademark), preferably sorbitan monooleate. Oil includes vegetable oil, mineral oil, animal oil, synthetic oil and silicone oil, preferably light liquid paraffin.

(8) Step of Preparation

The step of preparation is, in case of a polyvalent vaccine, a process of mixing compositions comprising the respective aforementioned structures derived from the specific microbial cells as obtained in the above steps. For instance, in case of a trivalent vaccine comprising as an active ingredient the aforementioned structures derived from *Salmonella Typhimurium, Salmonella Infantis* and *Salmonella Enteritidis*, a composition comprising the aforementioned structure derived from *Salmonella Typhimurium*, a composition comprising the aforementioned structure derived from *Salmonella Infantis* and a composition comprising the aforementioned structure derived from *Salmonella Enteritidis* are mixed together.

The obtained vaccine may be used alone as a *salmonella* vaccine for birds or used as a mixed vaccine in combination with at least one vaccine selected from the group consisting of vaccines against other viruses (e.g. infectious bronchitis virus, infectious bursal disease virus, avian encephalomyelitis virus, Egg drop syndrome virus, Newcastle disease virus, Avian reovirus, avian influenza virus, Marek's disease virus, infectious laryngotracheitis virus, avian pneumovirus, and fowlpox virus), bacteria (e.g. *Mycoplasma gallisepticum, Mycoplasma synoviae, Clostridium septicum, Clostridium perfringens, Campylobacter jejuni,* and *Campylobacter fetus*) and protozoa (e.g. *Leucocytozoon caulleryi, Eimeria tenella, Eimeria maxima,* and *Eimeria necatrix*).

In case of a polyvalent vaccine and a mixed vaccine, a ratio of the respective compositions comprising the aforementioned structure (EU ratio) may be either equal or a ratio of a specific composition may be increased or decreased.

The present invention is explained in more detail by means of the following Examples but is not limited thereto.

Example 1

(1) Preparation of Antigen
1) Step of Culture

On each 50 mL of LB medium (comprising sodium chloride 10 g, Bact Tryptone 10 g, Bact Yeast Extract 5 g in 1,000 mL of culture medium), *Salmonella Enteritidis* (hereinafter referred to as "SE"), *Salmonella Infantis* (hereinafter referred to as "SI"), and *Salmonella Typhimurium* (hereinafter referred to as "ST") were cultured (37° C., 16 to 24 hours, $4 \times 10^8$ to $4 \times 10^9$ CFU/mL).

2) Step of Inactivation

Formalin was added to the respective culture at 0.4% formalin for treatment at 37° C. for 16 hours to inactivate the cells.

3) Step of Release

The inactivated cells were subject to ultrasonic crushing or treated with phenol to release lipopolysaccharide.

Ultrasonic crushing (Branson, Sonifier 350) of the cells was carried out in ice water for 15 minutes. Then, centrifugation (TOMY SEIKO Co, Ltd., 10,000×g, 15 minutes) was performed and supernatant was used in the step of collection.

The phenol treatment of the cells was carried out by mixing 20 mL of the cell solution after formalin inactivation with an equivalent volume of a saturated phenol solution and heating the mixture at 68° C. for 15 minutes while stirring at every 3 minutes. Then, after the mixture was left to stand at 4° C. for 1 day, centrifugation (TOMY SEIKO Co, Ltd., 10,000×g, 15 minutes) was performed. For further removing impurities, supernatant was centrifuged (TOMY SEIKO Co, Ltd., 10,000×g, 15 minutes). Thereafter, supernatant was dialyzed with PBS for 3 days and used in the step of collection.

4) Step of Collection

Each 30 mL of supernatant was added to ET-clean L column (Chisso Corporation, catalogue No. 20015). After washing of the column with a phosphate buffer containing 0.15M NaCl (NaCl 8.76 g in 1,000 mL of solution), lipopolysaccharide was eluted with a phosphate buffer containing 2M NaCl (NaCl 117.54 g in 1,000 mL of solution).

(2) Determination of Endotoxin

A solution of the respective antigens diluted with distilled water and reference standard of CSE-L set (*E. coli* O113: endotoxin derived from H10) were added to a microplate. LAL reagent of Endospecy ES-50M Set (SEIKAGAKU BIOBUSINESS CORPORATION) was added. The plate was covered for the reaction at 37° C. for 30 minutes. A mixture of sodium nitrite/hydrochloric acid, an ammonium sulphamate solution, and a mixture of N-(1-naphtyl)ethylenediamine dihydrochloride/N-methyl-2-pyrrolidone in Toxicolor System DIA Set (SEIKAGAKU BIOBUSINESS CORPORATION) were added and the microplate was well shaken. Absorbance was measured at two wavelengths 545 nm and 630 nm (Molecular Devices Japan, VersaMax) to determine endotoxin unit.

(3) Step of Emulsification and Step of Preparation

Each 3.6 mL of the antigen solution was mixed and emulsified with 14.4 mL of oil adjuvant (a mixture of light liquid paraffin, sorbitan monooleate and polysorbate 80). An equivalent amount of the respective vaccines were mixed together to prepare a *salmonella* vaccine comprising three kinds of lipopolysaccharides (trivalent LPS vaccine). For said vaccine, a vaccine comprising each 54,000 EU/mL, a vaccine comprising each 5,400 EU/mL, and a vaccine comprising each 540 EU/mL, of lipopolysaccharides derived from SE, ST, or SI were prepared.

(4) Immunization Test

Each 0.5 mL of the respective vaccines was administered to 5-week old SPF chickens at the lower thigh muscle. As a control, a trivalent mixed whole-cells vaccine comprising inactivated whole cells of SE, ST, and SI was used. The trivalent mixed whole-cells vaccine was prepared by culturing the respective cells, inactivating the cells, diluting the cells with PBS at 54,000 EU/mL of lipopolysaccharide, and mixing and emulsifying the inactivated cells with oil adjuvant. A group with no administration of vaccine was also provided. The administration site was observed up till 10 weeks after administration and safety was assessed. Four weeks after immunization, the chicken were challenged by oral rout with *Salmonella* SE ($9.1 \times 10^9$ CFU/chicken), SI ($2.3 \times 10^9$ CFU/chicken), or ST ($1.2 \times 10^9$ CFU/chicken) to investigate effectiveness. For assessing effectiveness, feces were collected at 1, 4, 7, 10, and 14 days after challenge and the number of the shedding cells into cecal dropping was measured by the method described below.

(5) Measurement of Number of Cells

The collected feces were diluted with HTT medium at 20% emulsion and 50 μL of the emulsion was applied to DHL agar plate for culture (37° C., 16 to 24 hours). The next day, the number of the emerged colonies was counted to measure the number of cells in cecum feces (CFU/g). For those samples which gave no colony after this direct culture, enrichment culture was performed for 1 day and the number of cells was determined by the presence of colony (those samples which gave colony after this culture had the number of cells of 50 CFU/g). For those samples which gave no colony after enrichment culture for 1 day, delayed secondary culture was performed and the number of cells was determined by the presence of colony (those samples which gave colony after this culture had the number of cells of 10 CFU/g and those samples which gave no colony even after this culture had the number of cells of 0 CFU/g).

(6) Method of Assessment for Edema in Legs

The administration site was observed for 10 weeks and safety was assessed with swelling score of legs. For swelling score, Score 1 was light swelling (swelling at a portion of the lower thigh) at the administration site, Score 2 was moderate swelling (swelling at a whole of the lower thigh), and Score 3 was severe swelling (in addition to swelling at a whole of the lower thigh, dropsy is detected by palpation). Score was decided by visual observation and palpation.

(7) Results

Figure 3:
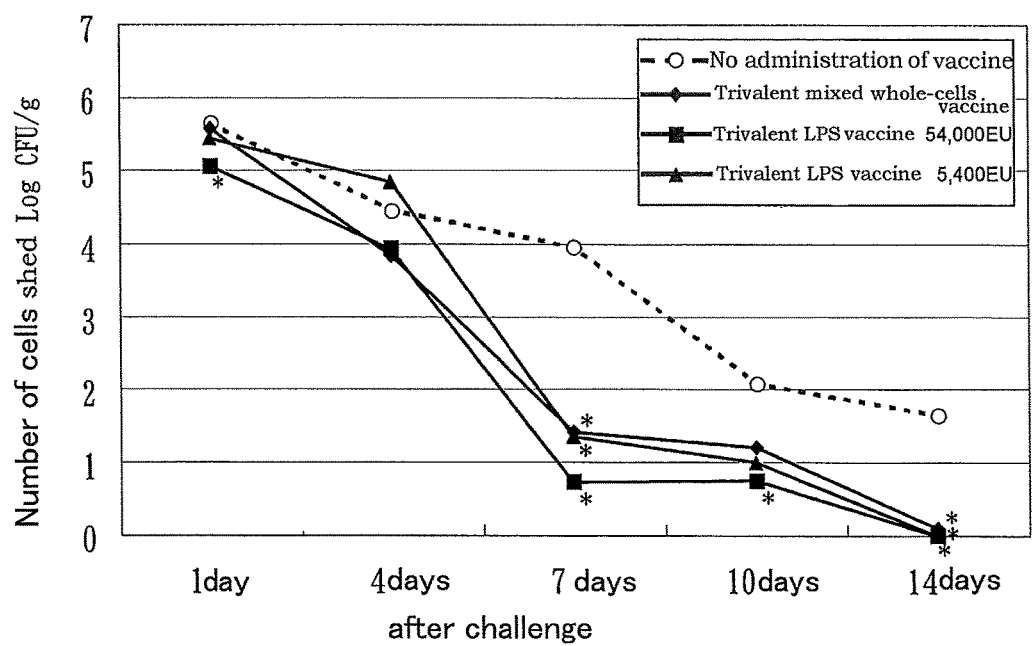
FIG. 3 shows the number of cells shed when a challenge test with *Salmonella Enteritidis* is carried out for trivalent LPS vaccine wherein the asterisk * shows a significant difference from control group ($p<0.05$).
Figure 4:
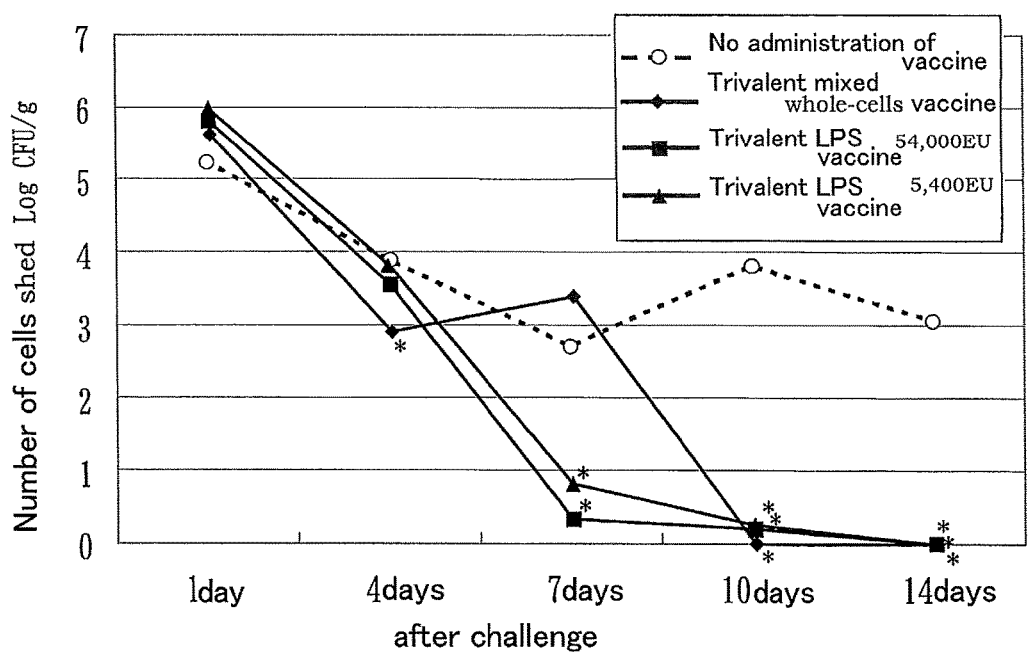
FIG. 4 shows the number of cells shed when a challenge test with *Salmonella Infantis* is carried out for trivalent LPS vaccine wherein the asterisk * shows a significant difference from control group (p<0.05).
Figure 5:
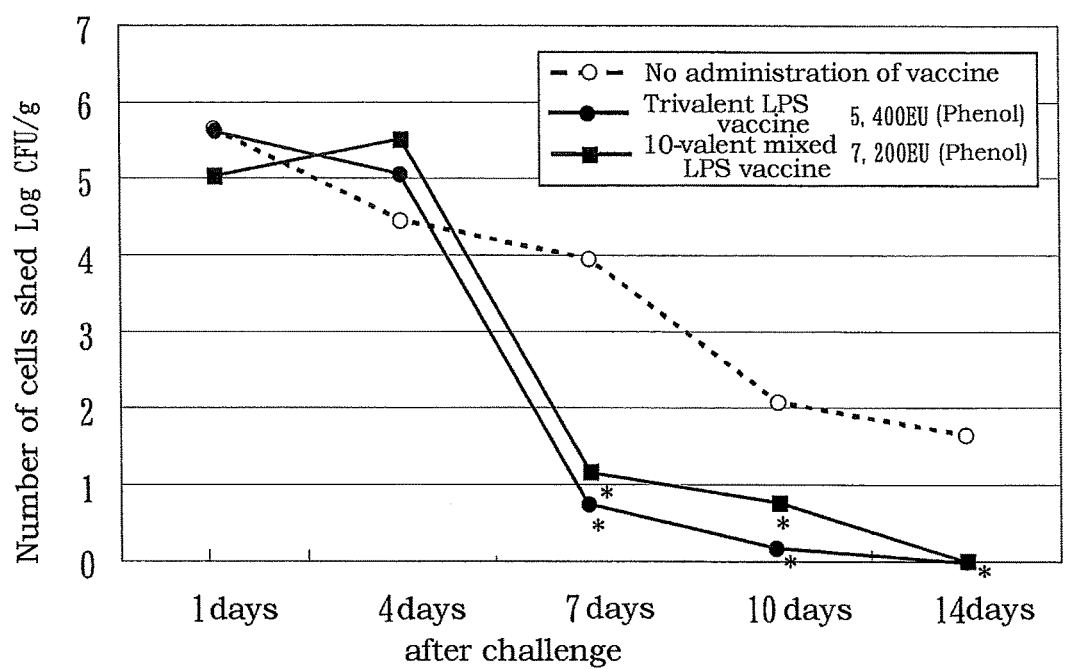
FIG. 5 shows the number of cells shed when a challenge test with *Salmonella Enteritidis* is carried out for 10-valent mixed LPS vaccine wherein the asterisk * shows a significant difference from control group (p<0.05).

The results of observation of swelling in legs are shown in FIG. 1. The results obtained after challenge with ST are shown in FIG. 2. The results obtained after challenge with SE are shown in FIG. 3. The results obtained after challenge with SI are shown in FIG. 4. As shown in FIG. 1, alleviation in swelling in legs was proved for the trivalent LPS vaccine as compared to the trivalent mixed whole cell vaccine. Swelling in legs was further alleviated for the trivalent LPS vaccine in which impurities such as proteins were further removed by the step of phenol extraction. With regard to effectiveness, the shedding of cells was reduced significantly in all the challenge tests with ST, SE and SI for the administration group of trivalent LPS vaccine as shown in FIG. 3, FIG. 4 and FIG. 5 to affirm effective of the trivalent LPS vaccine. The shedding of cells was also reduced in the administration group of trivalent LPS vaccine with phenol extraction to prove that a structure containing O-antigen (specifically, lipopolysaccharide) is useful as an antigen for a *salmonella* vaccine.

Example 2

(1) Preparation of Antigen

The vaccine prepared in Example 1 comprising each 54,000 EU/mL of lipopolysaccharides derived from SE, ST, or SI was mixed with OILVAX 7 (registered trademark; The Chemo-Sero-Therapeutic Research Institute; comprising infectious bronchitis virus Nerima strain, TM strain, *Mycoplasma gallisepticum*, Egg drop syndrome virus, and infectious coryza A and C (recombinant antigen)). The resultant mixture was 10-valent mixed LPS vaccine comprising each 7,200 EU/mL of lipopolysaccharides derived from SE, ST, or SI, $10^{8.4}$ EID$_{50}$/mL or more of Newcastle disease virus, $10^{6.4}$ EID$_{50}$/mL or more of infectious bronchitis virus Nerima strain, $10^{6.4}$ EID$_{50}$/mL or more of TM strain, $10^{7.4}$ EID$_{50}$/mL or more of *Mycoplasma gallisepticum*, $10^{6.7}$ EID$_{50}$/mL or more of Egg drop syndrome virus, and 2.4 μg/mL or more of infectious coryza A and C (recombinant antigen).

(2) Immunization Test

Each 0.5 mL of the 10-valent mixed LPS vaccine prepared above was administered to 5-week old SPF chicken at the lower thigh muscle. As a control, the administration group of OILVAX 7 or the trivalent LPS vaccine (each 5,400 EU/mL of lipopolysaccharide from SE, ST, and SI) and a group with no administration of vaccine were provided. Swelling in legs was observed up till 10 weeks after administration to assess safety. Four weeks after immunization, the chicken were challenged by oral rout with Salmonella SE ($9.1\times10^9$ CFU/chicken), or SI ($2.3\times10^9$ CFU/chicken) to investigate effectiveness. For assessing effectiveness, feces were collected at 1, 4, 7, 10, and 14 days after challenge and the number of the shedding cells into cecal dropping was measured by the method of measuring the number of cells described in Example 1. An extent of swelling was assessed as described in Example 1.

(3) Results

Figure 6:
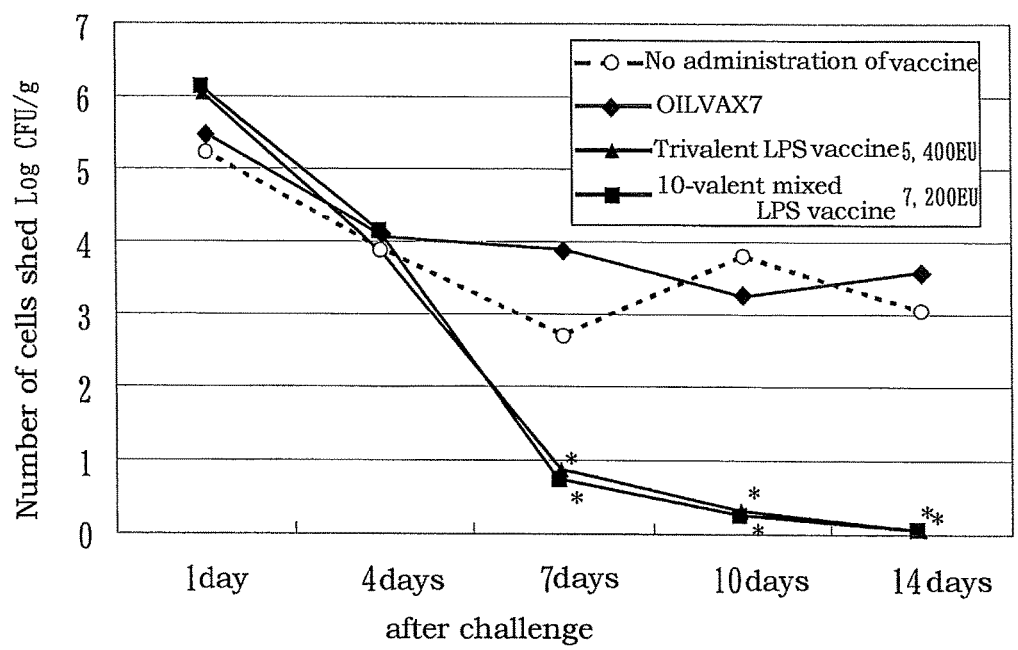
FIG. 6 shows the number of cells shed when a challenge test with *Salmonella Infantis* is carried out for 10-valent mixed LPS vaccine wherein the asterisk * shows a significant difference from control group (p<0.05).

The results of observation of swelling in legs are shown in FIG. 1. The results obtained after challenge with SE are shown in FIG. 5. The results obtained after challenge with SI are shown in FIG. 6. As shown in FIG. 1, alleviation in swelling in legs was proved for the 10-valent mixed LPS vaccine when lipopolysaccharide was further purified by adding the step of phenol extraction. As a result of observation of the injection site up till 10 weeks after immunization, no swelling problematic in the field causing dysstasia (Score 3) was seen for the 10-valent mixed LPS vaccine comprising lipopolysaccharide not treated with phenol to affirm safety of the 10-valent mixed LPS vaccine. With regard to effectiveness, the reduction in shedding of cells equivalent to the trivalent LPS vaccine was seen in the challenge tests with SE or SI to affirm effectiveness of the 10-valent mixed LPS vaccine.

INDUSTRIAL APPLICABILITY

A vaccine comprising as an active ingredient a structure containing O-antigen (e.g. lipopolysaccharide) derived from Gram-negative bacteria allows for reduction in side effects at the injection site. Besides, by mixing the aforementioned structures derived from a plurality of Gram-negative bacteria, it becomes possible to manufacture a polyvalent vaccine and a mixed vaccine without increasing an amount of injection.

The invention claimed is:

1. A composition comprising lipopolysaccharide from *Salmonella*,
   wherein the *Salmonella* is one or more *Salmonella* groups selected from the group consisting of O4, O7 and O9, and
   wherein the composition comprises at least one purified lipopolysaccharide O-antigen from *Salmonella Enteritidis, Salmonella Typhimurium*, and *Salmonella Infantis*, provided that said O-antigen is not comprised in a whole cell.

2. The composition of claim 1, further comprising at least one of an antigen from Newcastle disease virus, an antigen from avian infectious bronchitis virus, an antigen from *Mycoplasma gallisepticum*, an antigen from Egg drop syndrome virus, or an antigen from *Haemophilus paragallinarum*.

3. The composition of claim 1, comprising the O-antigen in an amount of at least 5,400 EU/ml.

4. The composition of claim 1, comprising the O-antigen in an amount of at least 54,000 EU/ml.

5. The composition of claim 1, comprising two of the purified lipopolysaccharide O-antigens.

6. The composition of claim 1, comprising three of the purified lipopolysaccharide O-antigens.

7. The composition of claim 1, further comprising an adjuvant.

8. The composition of claim 1, wherein the O-antigen is not bound to a carrier protein.

9. The composition of claim 1, wherein the O-antigen is bound to a carrier protein.

10. The composition of claim 9, wherein the carrier protein is selected from the group consisting of diphtheria toxoid (DT), tetanus toxoid (TT), cholera toxin (CT) and CRM197.

* * * * *